US012595242B2

(12) United States Patent
Lei et al.

(10) Patent No.: US 12,595,242 B2
(45) Date of Patent: Apr. 7, 2026

(54) PROCESS AND DEVICE FOR PREPARING TRIOXANE FROM METHANOL

(71) Applicants: CHENGDU ORGANIC CHEMICALS CO., LTD. CHINESE ACADEMY OF SCIENCES, Chengdu (CN); CHENGDU ZHONGKE CATALYSIS TECHNOLOGY CO., LTD., Chengdu (CN)

(72) Inventors: Qian Lei, Chengdu (CN); Linlin Liang, Chengdu (CN); Conger Deng, Chengdu (CN); Weixin Lei, Chengdu (CN); Honglin Chen, Chengdu (CN)

(73) Assignees: CHENGDU ORGANIC CHEMICALS CO., LTD. CHINESE ACADEMY OF SCIENCES, Chengdu (CN); CHENGDU ZHONGKE CATALYSIS TECHNOLOGY CO., LTD., Chengdu (CN)

( * ) Notice: Subject to any disclaimer, the term of this patent is extended or adjusted under 35 U.S.C. 154(b) by 849 days.

(21) Appl. No.: 17/789,242

(22) PCT Filed: Feb. 20, 2021

(86) PCT No.: PCT/CN2021/077066

§ 371 (c)(1),
(2) Date: Jun. 27, 2022

(87) PCT Pub. No.: WO2022/095307

PCT Pub. Date: May 12, 2022

(65) Prior Publication Data

US 2023/0069011 A1 Mar. 2, 2023

(30) Foreign Application Priority Data

Nov. 5, 2020 (CN) ......................... 202011222860.1

(51) Int. Cl.
*C07D 323/06* (2006.01)

(52) U.S. Cl.
CPC ................................. *C07D 323/06* (2013.01)

(58) Field of Classification Search
CPC .................................................... C07D 323/06
USPC .......................................................... 549/368
See application file for complete search history.

(56) References Cited

FOREIGN PATENT DOCUMENTS

| | | | | |
|---|---|---|---|---|
| CN | 1169725 | A | 1/1998 | |
| CN | 1249047 | C | 4/2006 | |
| CN | 103333059 | A | 10/2013 | |
| CN | 101896478 | B | 9/2014 | |
| CN | 102702167 | B | 1/2015 | |
| CN | 103420974 | B | 2/2015 | |
| CN | 105582961 | A | 5/2016 | |
| CN | 110437045 | A | 11/2019 | |
| CN | 111672516 | A | 9/2020 | |
| CN | 111689840 | A | 9/2020 | |
| CN | 111808067 | A | 10/2020 | |
| CN | 112174931 | A | 1/2021 | |
| EP | 3263552 | A1 * | 1/2018 | .............. C07J 51/00 |
| FR | 2909089 | A1 * | 5/2008 | ........... C07C 213/02 |
| WO | 2014017203 | A1 | 1/2014 | |

* cited by examiner

*Primary Examiner* — Taofiq A Solola
(74) *Attorney, Agent, or Firm* — Bayramoglu Law Offices LLC

(57) ABSTRACT

A process for preparing trioxane from methanol includes: step 1: subjecting a mixture of methanol and methylal to a reaction to obtain formaldehyde, and absorbing the formaldehyde with water to obtain a concentrated formaldehyde aqueous solution; step 2: subjecting the concentrated formaldehyde aqueous solution to cyclization to obtain a mixture containing trioxane, and passing the mixture through a trioxane concentration tower to obtain a crude trioxane product; step 3: converting a by-product and unreacted formaldehyde in the crude trioxane product into methanol, conducting dehydration through a membrane dehydration process, and subjecting a retentate to dealcoholization to obtain purified trioxane; and step 4: subjecting the remaining streams to reactive distillation to obtain a mixture of methanol and methylal at a top- and water at a bottom of the reactive distillation tower; returning the mixture of methanol and methylal to step 1; and returning or discharging the water.

9 Claims, 1 Drawing Sheet

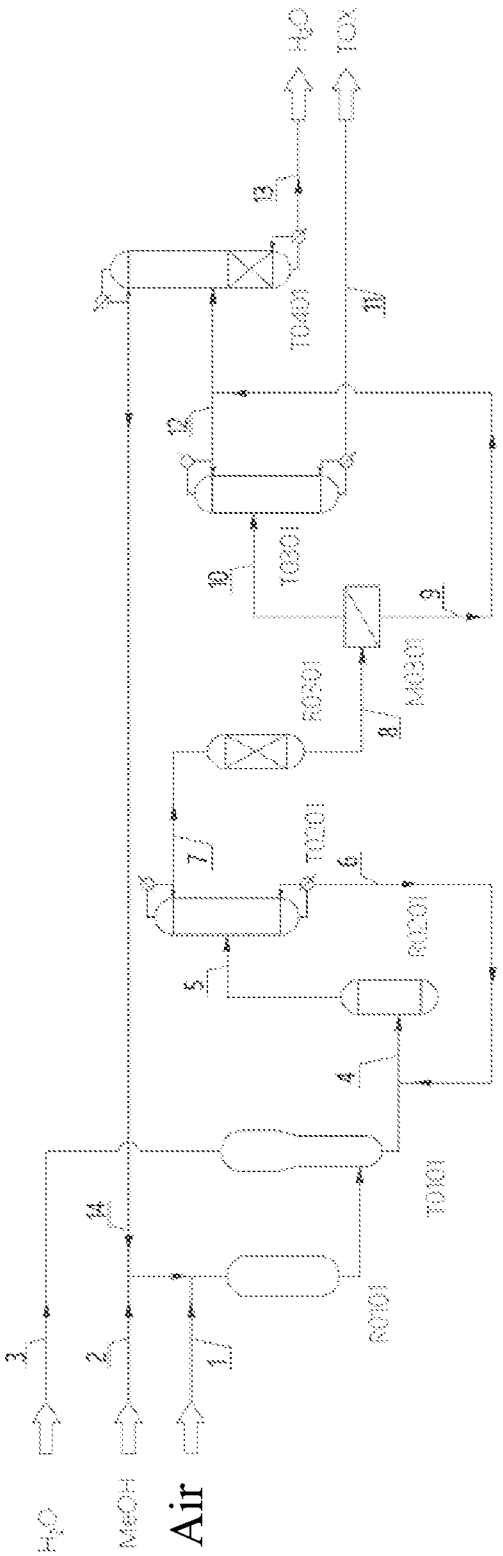
Air
MeOH
$H_2O$
$H_2O$
TOX

PROCESS AND DEVICE FOR PREPARING TRIOXANE FROM METHANOL

CROSS REFERENCE TO THE RELATED APPLICATIONS

This application is the national phase entry of International Application No. PCT/CN2021/077066, filed on Feb. 20, 2021, which is based upon and claims priority to Chinese Patent Application No. 202011222860.1, filed on Nov. 5, 2020, the entire contents of which are incorporated herein by reference.

TECHNICAL FIELD

The present disclosure relates to the field of chemical production processes, and in particular to a process and device for preparing trioxane from methanol.

BACKGROUND

Polyoxymethylene (POM), also known as acetal or polyoxymethylene, is an engineering thermoplastic with excellent comprehensive performance and is one of the five major engineering plastics. POM shows mechanical properties closest to that of metal materials among engineering plastics, hence, such polymers are used to serve as an alternative to metals. Trioxane and dioxolane are key monomers for the production of POM, and their purities directly affect the performance of POM. Therefore, a total amount of impurities in trioxane or dioxolane is required to be less than 100 ppm.

In the currently synthesis processes for trioxane, a formaldehyde solution with a concentration of greater than 60% is subjected to a reaction under the catalysis of sulfuric acid in a reactor to obtain trioxane, and a resulting reaction solution is subjected to concentration by rectification, extraction with benzene, neutralization (formic acid removal), and purification in subsequent rectification towers to obtain a pure trioxane product.

Due to the low equilibrium conversion rate during trioxane synthesis, there is a large amount of unreacted formaldehyde in a trioxane solution during separation. Unreacted formaldehyde will condense and polymerize with water, methanol, and formaldehyde itself to produce hemiacetals, acetals, and formaldehyde polymers. Some hemiacetals, acetals, and formaldehyde polymers have a similar relative volatility to trioxane and thus cannot be separated by an ordinary separation method. Currently, a synthetic product is preliminarily separated generally by crystallization or extraction, and then refined by rectification. A production method of high-purity trioxane is disclosed in CN1169725A (published on Jan. 7, 1998) by Asahi Kasei Corp. In the production method, a formaldehyde aqueous solution (as a raw material) is subjected to a reaction in the presence of an acidic catalyst; a resulting reaction solution is subjected to extraction to obtain a first trioxane mixture including $CH_3O(CH_2O)_nCH_3$ (low-polyformal), formaldehyde, methanol, formic acid, and benzene (extracting agent); the first trioxane mixture is subjected to rectification to remove benzene and low-boiling-point components, such that a second trioxane mixture including $CH_3O(CH_2O)_nCH_3$ (low-polyformal) is obtained at a bottom of a rectification tower; and the second trioxane mixture is allowed to contact a solid acidic catalyst in the presence of water for decomposing the low-polyformal, and then subjected to extraction and rectification to obtain trioxane. A trioxane refinement system consisting of a vapor-liquid benzene extraction tower, a benzene recovery tower, and a trioxane rectification tower is disclosed in CN103420974B (published on Jul. 29, 2013) by China SedinNingbo Engineering Co., Ltd. An alkali-free process for separating high-purity trioxane is disclosed in CN110437045A (published on Aug. 26, 2019) by Jiangsu Dolton Chemical Technology Co., Ltd. In the alkali-free process, crude trioxane from a synthesis unit is subjected to extraction in an extraction tank, then an extraction phase composed of trioxane and benzene is fed into a water-washing tower to obtain trioxane without formaldehyde, and the trioxane without formaldehyde is subjected to conventional rectification for low and high-boiling-point component removal to obtain polymer-grade trioxane.

However, the above separation solution still fails to produce ultra-pure or nearly 100%-pure trioxane, and due to the introduction of a new solvent during the extraction, a separation system is more complicated, such that the energy consumption is increased, and it is difficult to recover diluted formaldehyde solution, especially since a separate diluted aldehyde solution recovery unit is often required for recovery.

In addition, no matter what catalytic system is used in the synthesis of trioxane, there are a series of side reactions. The most important among these side reactions is a disproportionation reaction of formaldehyde (Cannizzaro), producing methanol and formic acid.

$$2CH_2O + H_2O \xrightleftharpoons{\text{cat.}} CH_3OH + HCOOH$$

The formic acid produced by this side reaction is corrosive, and thus an increase in a formic acid content will cause corrosion on equipment and affect a service life of the equipment. Methanol and formic acid may be further esterified under the action of a catalyst to produce methyl formate.

$$CH_3OH + HCOOH \xrightleftharpoons{\text{cat.}} HCOOCH_3 + H_2O$$

Formaldehyde may also undergo a Tischenko reaction to produce methyl formate $$2CH_2O \xrightleftharpoons{\text{cat.}} HCOOCH_3$$

A mixture of trioxane, formaldehyde, and water obtained by reactive distillation further includes formic acid, methyl formate, and methanol generated by side reactions, resulting in a multi-component azeotrope in which the components are difficult to separate. Due to the presence of formaldehyde, a local formaldehyde concentration in a separation unit is too high, such that a formaldehyde polymer is easily generated to cause the blockage of equipment and pipelines in a rectification tower. In addition, the presence of formic acid can easily cause corrosion on equipment and pipelines. In order to remove these impurities, an alkaline adsorbent can be used to remove formic acid in a condensation product through adsorption, then an adsorbent such as molecular sieve can be used to remove $H_2O$ through adsorption, and then the product is separated and purified by rectification. For example, a refinement method is disclosed in CN1249047C (published on Apr. 5, 2006) by PATENES NOVEDADES SA Y. In the refinement method, an aqueous mixture of trioxane and formaldehyde obtained from a reactor is subjected to a reaction with urea to obtain a gas phase and a liquid phase, the gas phase is an azeotrope composed of formaldehyde-free water and trioxane, and the liquid phase is a urea-aldehyde precondensate obtained from a reaction of formaldehyde and urea; which is then used for the synthesis of a urea-formaldehyde glue or resin. A method for removing formic acid is disclosed in CN102702167B (published on May 11, 2012) by Beijing Risun Chemical Industry Technology Research institute Co., Ltd., where a gas mixture including formic acid, trioxane, formaldehyde, and water from an outlet of a reactor is washed with a buffer of a carbonate or phosphate to remove formic acid. BASF has made great efforts in the removal of formic acid, and discloses a method for removing formic acid in CN101896478B (published on Nov. 24, 2010), where a physical (adsorption) or chemical (for example, a tertiary amine or imine is added to convert formic acid into a salt under the action of a catalyst, and the generated salt is removed at a bottom of a rectification tower) process is added to the conventional pressure swing distillation (PSD) process to remove formic acid.

This separation process is simple and feasible in theory, but due to the complexity and variability of a formaldehyde-containing system in actual operations, the adsorption deacidification and dehydration process is accompanied by the adsorption or conversion of formaldehyde (disproportionation, saccharification, discoloration, and the like). Moreover, because formaldehyde exists in the form of methylene glycol or hemiacetal, the conventional adsorption dehydration method cannot remove water combined with formaldehyde, and thus cannot fundamentally solve the problems that components in a multi-component azeotrope are difficult to separate and pipelines are easily blocked due to self-polymerization.

In summary, the existing technologies often have the following shortcomings: When the extractive rectification is adopted to separate impurities, many trace impurities will inevitably be introduced. When an alkaline adsorbent is adopted to adsorb and remove formic acid or formaldehyde in a product or to convert formaldehyde into a polymer, the desorbed formaldehyde and formic acid cannot be directly recycled, resulting in increased material consumption; and after the adsorbent adsorbs formaldehyde, a local formaldehyde concentration of the adsorbent is easy to increase, and the polymerization of formaldehyde reduces the performance of the adsorbent. Therefore, the existing technologies cannot fundamentally solve the problems of multi-component azeotropy, blockage caused by self-polymerization, low trioxane purity, and high material and energy consumption per unit product.

SUMMARY

In view of the above-mentioned problems, the present disclosure provides a process for preparing and refining trioxane, wherein one from the group consisting of or a mixture of methanol and methylal is used as a raw material and subjected to oxidation and absorption to obtain a concentrated formaldehyde aqueous solution; the concentrated formaldehyde aqueous solution is subjected to cyclization under an action of a solid acidic catalyst, a mixture with concentrated trioxane is separated and subjected to catalytic refinement to obtain a mixture of methanol, water, and trioxane, and the mixture of methanol, water, and trioxane is subjected to dehydration through pervaporation and then to methanol removal through rectification to obtain pure trioxane, in the dehydration process of pervaporation, low-boiling-point components at a permeate side and in the methanol removal tower are catalytically converted in a recovery section, and a mixture of methylal and methanol obtained at a top of a reactive distillation tower is returned to the concentrated formaldehyde production section; and water obtained at a bottom of the reactive distillation tower can be discharged from a system or returned to a formaldehyde absorption unit.

The present disclosure provides a process for preparing trioxane from methanol, including the following steps:

step 1: subjecting a mixture of methanol and methylal to a reaction under an action of an oxidation catalyst to obtain formaldehyde, and absorbing the formaldehyde with water to obtain a concentrated formaldehyde aqueous solution;

step 2: in a trioxane synthesis reactor, subjecting the concentrated formaldehyde aqueous solution to cyclization under an action of a cyclization catalyst to obtain a mixture containing trioxane, and passing the mixture through a trioxane concentration tower for rectification and concentration to obtain a crude trioxane product;

step 3: converting a by-product and unreacted formaldehyde in the crude trioxane product into methanol through catalytic refinement, conducting dehydration through a membrane dehydration process, and subjecting a retentate to dealcoholization to obtain purified trioxane; and step 4 after the purified trioxane is separated, combining the remaining streams of the entire process to obtain a mixture including methanol, water, and a small amount of trioxane, and subjecting the mixture including methanol, water, and a small amount of trioxane to reactive distillation to obtain a mixture of methanol and methylal at a top of a reactive distillation tower and water at a bottom of the reactive distillation tower; returning the mixture of methanol and methylal to step 1, and returning the water to a formaldehyde absorption tower, or discharging the water from a system.

In step 1, a concentration of formaldehyde in the concentrated formaldehyde aqueous solution may be greater than 50%, and the concentrated formaldehyde aqueous solution may be prepared by an iron-molybdenum method, with one or more from the group consisting of methanol and methylal as a raw material.

In step 2, the cyclization under an action of a cyclization catalyst may be conducted at a reaction temperature of 80° C. to 150° C. and a reaction pressure of −0.1 MPa to 0.3 MPa. The cyclization catalyst may be preferably an acidic catalyst, the acidic catalyst may be preferably a solid acidic catalyst, and the solid acidic catalyst may be one or more selected from the group consisting of a resin, a molecular sieve, a supported ionic liquid, and aluminum oxide.

In step 2, the trioxane synthesis reactor may be a separate tank reactor or fixed bed reactor, or may be integrated with the trioxane concentration tower and arranged at a bottom of or inside the trioxane concentration tower. When a tank reactor is adopted and arranged at a bottom of the trioxane concentration tower, an amount of the cyclization catalyst may be 0.1% to 20% of a reaction solution; and when a fixed bed reactor is adopted and arranged inside the trioxane concentration tower, a volume space velocity of feeding may be 0.2 $h^{-1}$ to 10 $h^{-1}$. A discharge port may be formed at a bottom of the trioxane synthesis reactor, which can discharge a part of reactants to reduce a formic acid content in the reactor, and can also discharge a part of the deactivated cyclization catalyst; and a cyclization catalyst supplementation inlet may be formed at an inlet of the trioxane synthesis reactor.

In step 2, the rectification and concentration is conducted in the trioxane concentration tower; an inlet may be formed at a middle part or a bottom of the trioxane concentration tower to receive the gas phase from the trioxane synthesis reactor, and the trioxane concentration tower may be a plate tower, a dividing wall tower, or a packed tower.

In step 2, through rectification and concentration, a trioxane concentrate stream with a trioxane content of greater than 45% and a formaldehyde content of less than 15% may be obtained at a top of the trioxane concentration tower, a formaldehyde aqueous solution stream at a bottom of the trioxane concentration tower may have a trioxane content of less than 1%, and an operating pressure of the trioxane concentration tower may be −0.1 MPa to 0.2 MPa.

In step 3, the catalytic refinement may be conducted with a refinement catalyst, and the refinement catalyst may have bifunctional sites of an acidic site and a hydrogenation active site. The acidic site causes the methylal and formaldehyde polymer to be decomposed into formaldehyde, methanol, or the like.

The hydrogenation active site can catalyze the conversion of formaldehyde, formic acid, methyl formate, and the like into methanol.

A preparation method of the refinement catalyst may include: loading a hydrogenation active component on an acidic active component; or mechanically mixing the hydrogenation active component and the acidic active component, and forming by compressing; or mechanically mixing the hydrogenation active component and the acidic active component, adding a binder, and forming by extrusion.

In step 3, an active component for the hydrogenation active site of the refinement catalyst may be a Ni-based catalyst system, and the Ni-based catalyst system may include one or more components selected from the group consisting of $Al_2O$, $SiO_2$, activated carbon, molecular sieve, Zn, K, Mg, Cu, and Cr. As used herein, the Ni-based catalyst system refers to a catalyst that includes nickel oxide as a carrier and other elements or substances.

In step 3, an active component for the acidic site of the refinement catalyst may include one or more components selected from the group consisting of $Al_2O_3$, $SiO_2$, activated carbon, and molecular sieve. In addition, a content of the active component for the acidic site may be 0.1% to 10%. When the content of the active component for the acidic site is higher than 10%, cyclic formaldehyde derivatives are easily decomposed.

In step 3, under a hydrogen atmosphere, the by-product and the unreacted formaldehyde in the crude trioxane product may be converted into methanol through the catalytic refinement.

In step 3, a volume ratio of the hydrogen to the impurity-containing crude trioxane product may be is 1:1 to 100:1 and preferably 1:1 to 50:1.

In step 3, the catalytic refinement may be conducted in a fixed bed reactor.

In step 3, the catalytic refinement may be conducted at a reaction temperature of 30° C. to 200° C. and preferably 80° C. to 150° C., a reaction pressure of 0 MPa to 5 MPa and preferably 0 MPa to 2 MPa, and a reaction space velocity of 0.1 $h^{-1}$ to 10 $h^{-1}$ and preferably 0.5 $h^{-1}$ to 5 $h^{-1}$. The catalytic refinement may be conducted in an atmosphere created by one or more selected from the group consisting of hydrogen, nitrogen, and argon.

In step 3, a methanol solvent may be added to the crude trioxane product before the catalytic refinement.

In step 3, after the catalytic refinement, a refined trioxane stream may be subjected to dehydration with a membrane module, preferably through pervaporation or steam permeation, such that a mixture of trioxane and methanol with a water content of less than 0.1% is obtained at a retentate side.

In step 3, a membrane used in the dehydration membrane module may be a water-permeable molecular sieve membrane; the dehydration at the retentate side may be conducted at a temperature of 80° C. to 150° C. and a dehydration pressure of 0.1 MPa to 1.0 MPa; a pressure at a permeate side may be −0.05 MPa to −0.1 MPa; and the trioxane at the permeate side can be recovered through rectification and returned to an inlet of a dehydration membrane module unit, and water may be separated.

In step 3, methanol may be separated through rectification in a trioxane dealcoholization tower, and the trioxane dealcoholization tower may be a plate tower, a dividing wall tower, or a packed tower.

In step 4, the reactive distillation may be conducted in a recovery and reactive distillation tower; and a reactor may be integrated with the recovery and reactive distillation tower and arranged at a bottom of or inside the recovery and reactive distillation tower, and a volume space velocity of feeding may be 0.5 $h^{-1}$ to 50 $h^{-1}$.

In step 4, in the recovery and reactive distillation tower, a catalyst may be preferably an acidic catalyst, and the acidic catalyst may include one or more selected from the group consisting of a molecular sieve, a resin, and aluminum oxide; a reaction may be conducted at a reaction temperature of 30° C. to 200° C. and a reaction pressure of 0 MPa to 1.5 MPa; and under the action of the acidic catalyst, trioxane can react with methanol to generate methylal.

The present disclosure provides a device for preparing trioxane from methanol, including:

a methanol oxidation section to prepare formaldehyde: a methanol oxidation reactor and a formaldehyde absorption tower;

a crude trioxane product synthesis section: a trioxane synthesis reactor and a trioxane concentration tower;

a trioxane refinement and separation section: a trioxane refinement reactor, a trioxane dehydration membrane module, and a trioxane dealcoholization tower; and a recovery section: recovery and reactive distillation tower.

In the methanol oxidation section to prepare formaldehyde, a discharge port of the methanol oxidation reactor may be connected to a feed port of the formaldehyde absorption tower.

In the crude trioxane product synthesis section, a cyclization catalyst may be pre-filled in the trioxane synthesis reactor.

In the crude trioxane product synthesis section, the cyclization catalyst may be preferably an acidic catalyst, the acidic catalyst may be preferably a solid acidic catalyst, and the solid acidic catalyst may be one or more selected from the group consisting of a resin, a molecular sieve, a supported ionic liquid, and aluminum oxide.

In the crude trioxane product synthesis section, the trioxane synthesis reactor may be arranged at a bottom of or inside the trioxane concentration tower.

The trioxane synthesis reactor may be a separate tank reactor or fixed bed reactor and may be integrated with the trioxane concentration tower. When a tank reactor is adopted and arranged at a bottom of the trioxane concentration tower, an amount of the cyclization catalyst may be 0.1% to 20% of a reaction solution; and when a fixed bed reactor is adopted and arranged inside the trioxane concentration tower, a volume space velocity of feeding may be 0.2 $h^{-1}$ to 10 $h^{-1}$. A discharge port may be formed at a bottom of the trioxane synthesis reactor, which can discharge a part of reactants to reduce a formic acid content in the reactor, and can also discharge a part of the deactivated cyclization catalyst; and a cyclization catalyst supplementation inlet may be formed at an inlet of the trioxane synthesis reactor.

In the crude trioxane product synthesis section, the concentration is conducted in the trioxane concentration tower; and an inlet may be formed at a middle part or a bottom of the trioxane concentration tower to receive the gas phase from the trioxane synthesis reactor.

In the crude trioxane product synthesis section, the trioxane concentration tower may have two discharge ports, among which a discharge port at the bottom may lead to a feed port of the trioxane synthesis reactor. The trioxane concentration tower may be a plate tower, a dividing wall tower, or a packed tower.

In the trioxane refinement and separation section, a discharge port of the trioxane refinement reactor may be connected to the trioxane dehydration membrane module.

In the trioxane refinement and separation section, a refinement catalyst may be filled in the trioxane refinement reactor.

The catalytic refinement may be conducted with a refinement catalyst, and the refinement catalyst may have bifunctional catalytic sites of an acidic site and a hydrogenation active site. The acidic site causes the methylal and formaldehyde polymer to be decomposed into formaldehyde, methanol, or the like.

The hydrogenation active site can catalyze the conversion of formaldehyde, formic acid, methyl formate, and the like into methanol.

A preparation method of the refinement catalyst may include: loading a hydrogenation active component on an acidic active component; or mechanically mixing the hydrogenation active component and the acidic active component, and forming by compressing, or mechanically mixing the hydrogenation active component and the acidic active component, adding a binder, and forming by extrusion.

An active component for the hydrogenation active site of the refinement catalyst may be a Ni-based catalyst system, and the Ni-based catalyst system may include one or more components selected from the group consisting of $Al_2O_3$, $SiO_2$, activated carbon, molecular sieve, Zn, K, Mg, Cu, and Cr. As used herein, the Ni-based catalyst system refers to a catalyst that includes nickel oxide as a carrier and other elements or substances.

An active component for the acidic site of the refinement catalyst may include one or more components selected from the group consisting of $Al_2O_3$, $SiO_2$, activated carbon, and molecular sieve. In addition, a content of the active component for the acidic site may be 0.1% to 10%. When the content of the active component for the acidic site is higher than 10%, cyclic formaldehyde derivatives are easily decomposed.

In the trioxane refinement and separation section, the catalytic refinement may be conducted in a fixed bed reactor.

In the trioxane refinement and separation section, the catalytic refinement may be conducted at a reaction temperature of 30° C. to 200° C. and preferably 80° C. to 150° C., a reaction pressure of 0 MPa to 5 MPa and preferably 0 MPa to 2 MPa, and a reaction space velocity of 0.1 $h^{-1}$ to 10 $h^{-1}$ and preferably 0.5 $h^{-1}$ to 5 $h^{-1}$. The catalytic refinement may be conducted in an atmosphere created by one or more selected from the group consisting of hydrogen, nitrogen, and argon.

In the trioxane refinement and separation section, a retentate side of the trioxane dehydration membrane module may be connected to the trioxane dealcoholization tower, and a water-based permeate stream may be obtained at a permeate side.

In the trioxane refinement and separation section, a membrane used in the dehydration membrane module may be a water-permeable molecular sieve membrane; the dehydration at the retentate side may be conducted at a temperature of 80° C. to 150° C. and a dehydration pressure of 0.1 MPa to 1.0 MPa; a pressure at a permeate side may be −0.05 MPa to −0.1 MPa; and the trioxane at the permeate side can be recovered through rectification and returned to an inlet of a dehydration membrane module unit, and water may be separated.

In the trioxane refinement and separation section, methanol may be separated through rectification in a rectification tower, and the rectification tower may be a plate tower, a dividing wall tower, or a packed tower.

In the trioxane refinement and separation section, the trioxane dealcoholization tower may have two discharge ports, among which a discharge port at a top may lead to the recovery and reactive distillation tower and a trioxane product may be obtained from a discharge port at a bottom.

In the recovery section, the reactive distillation may be conducted in a recovery and reactive distillation tower; and a reactor may be integrated with the rectification tower and arranged at a bottom of or inside the rectification tower, and a volume space velocity of feeding may be 0.5 $h^{-1}$ to 50 $h^{-1}$.

In the recovery section, in the recovery and reactive distillation tower, a catalyst may be preferably an acidic catalyst, and the acidic catalyst may include one or more selected from the group consisting of a molecular sieve, a resin, and aluminum oxide; a reaction may be conducted at a reaction temperature of 30° C. to 200° C. and a reaction pressure of 0 MPa to 1.5 MPa; and under the action of the acidic catalyst, trioxane can react with methanol to generate methylal.

In the recovery section, the recovery and reactive distillation tower may have two discharge ports, among which a discharge port at a top may lead to the methanol oxidation reactor and a water-based stream may be obtained from a discharge port at a bottom.

Beneficial Effects

The present disclosure solves the problem that many by-products difficult to separate are produced in a trioxane synthesis process, and reduces an impurity content to improve the purity and quality of a trioxane product. The production of diluted aldehyde solution in the separation process is avoided through refinement, and through the combination with a membrane separation technology, the separation efficiency is improved and the energy consumption of separation is reduced. The utilization of raw materials in the entire process is improved by adopting a circulating process.

The present disclosure provides a trioxane synthesis process, where impurities such as formaldehyde, formic acid, methyl formate, methylal, and formaldehyde polymer are converted into methanol through catalytic refinement, which achieves the purposes of aldehyde removal, acid removal, and ester removal and makes the subsequent separation operation easy.

The present disclosure avoids the blockage of pipelines and equipment such as rectification tower in the subsequent separation process, reduces the corrosion to subsequent pipelines and equipment, and avoids the occurrence of a multi-component azeotrope in the system.

Compared with the traditional absorption, adsorption, and extraction processes, the catalytic refinement process in the present disclosure leads to no waste liquids and solids, and is environmentally friendly. Moreover, formaldehyde, formic acid, and methyl formate are converted into methanol through the catalytic refinement, and the methanol is then used for formaldehyde production, which improves the atomic utilization. In addition, no diluted aldehyde solution is produced in the entire process, which avoids the disadvantages of high energy consumption and heavy pollution caused by the recovery of diluted aldehyde solution.

BRIEF DESCRIPTION OF THE DRAWINGS

The accompanying drawing illustrates exemplary implementations of the present disclosure, and is intended to explain the principle of the present disclosure together with the description thereof. The accompanying drawing is provided to provide a further understanding of the present disclosure, and is included in and constitute part of the specification.

FIGURE is a schematic diagram illustrating a process flow of the process for preparing trioxane from methanol according to the present disclosure.

REFERENCE NUMERALS

R0101 represents a methanol oxidation reactor, T0101 represents a formaldehyde absorption tower, R0201 represents a trioxane synthesis reactor, T0201 represents a trioxane concentration tower, R0301 represents a trioxane refinement reactor, M0301 represents a trioxane dehydration membrane module, T0301 represents a trioxane dealcoholization tower, and T0401 represents a recovery and reactive distillation tower.

DETAILED DESCRIPTION OF THE EMBODIMENTS

The present disclosure is described in further detail below with reference to the accompanying drawing and implementations. It should be understood that the specific implementations described herein are merely intended to explain the related content, rather than to limit the present disclosure. It should also be noted that, for convenience of description, only the parts related to the present disclosure are shown in the accompany drawing.

It should be noted that the implementations or the features in the implementations of the present disclosure may be combined with each other in a non-conflicting manner. The present disclosure is described in detail below with reference to the accompanying drawing and implementations.

The preparation process of the present disclosure includes a methanol oxidation section to prepare formaldehyde, a crude trioxane product synthesis section, a trioxane refinement and separation section, and a recovery section, where

- the methanol oxidation section to prepare formaldehyde includes a methanol oxidation reactor R0101 and a formaldehyde absorption tower T0101;
- the crude trioxane product synthesis section includes a trioxane synthesis reactor R0201 and a trioxane concentration tower T0201;
- the trioxane refinement and separation section includes a trioxane refinement reactor R0301, a trioxane dehydration membrane module M0301, and a trioxane dealcoholization tower T0301; and
- the recovery section includes a recovery and reactive distillation tower T0401.

In the methanol oxidation reactor R0101, a mixture of methanol and methylal (a methanol stream 2 and a circulated stream 14) is subjected to evaporation, mixed with air (a material 1), and then subjected to a reaction under the action of an iron-molybdenum oxidation catalyst to produce formaldehyde, and the formaldehyde is absorbed by a water stream 3 in the formaldehyde absorption tower T0101 to obtain a formaldehyde aqueous solution. The formaldehyde aqueous solution is mixed with the formaldehyde aqueous solution stream 6 at a bottom of the trioxane concentration tower to obtain a trioxane synthesis stream 4.

A ZSM-5 molecular sieve catalyst is pre-filled in the trioxane synthesis reactor R0201, and the trioxane synthesis stream 4 quickly reaches a reaction equilibrium under the action of the ZSM-5 molecular sieve catalyst. Because a trioxane concentration in a gas phase is higher than a trioxane concentration in a liquid phase in the reactor and the gas phase is collected from an outlet, the reaction proceeds in a positive reaction direction. A gas phase stream 5 collected from the outlet of the trioxane synthesis reactor includes by-products of the trioxane synthesis reaction such as methanol, methyl formate, methylal, and formic acid, and unreacted formaldehyde.

The gas phase stream 5 collected from the outlet of the trioxane synthesis reactor is subjected to separation in the trioxane concentration tower T0201, such that a trioxane concentrate stream 7 is obtained at a top of the trioxane concentration tower, and a formaldehyde aqueous solution stream 6 is obtained at a bottom of the trioxane concentration tower and is returned to the trioxane synthesis reactor R0201.

The trioxane concentrate stream 7 including by-products and unreacted formaldehyde is subjected to catalytic refinement under a hydrogen atmosphere in a fixed bed reactor, such that methyl formate, methylal, formic acid, and formaldehyde are converted into methanol under the action of the $Ni/Al_2O_3$ refinement catalyst. After the catalytic refinement, a refined trioxane stream 8 is obtained for separation.

In the trioxane dehydration membrane module M0301, the refined trioxane stream 8 is subjected to pervaporation through a NaA molecular sieve membrane to obtain a water-free trioxane mixture stream 10 at a retentate side and a water-based permeate stream 9 at a permeate side.

The water-free trioxane mixture stream 10 enters the trioxane dealcoholization tower T0301 for methanol separation to obtain a pure trioxane stream with an impurity content of less than 100 ppm at a bottom of the trioxane dealcoholization tower and a trioxane-containing methanol solution stream 12 at a top of the trioxane dealcoholization tower.

The trioxane-containing methanol solution stream 12 and the permeate stream 9 are mixed and then allowed to pass through the recovery and reactive distillation tower R0401 to obtain a mixture stream 14 of methanol and methylal at a top of the recovery and reactive distillation tower. This stream is returned to an inlet of the methanol oxidation reactor and then recycled as a raw material for formaldehyde production. A pure water stream 13 is obtained at a bottom of the recovery and reactive distillation tower, which can be recycled as an absorption liquid of the formaldehyde absorption tower.

EXAMPLES

Example 1

The preparation process was conducted by the methanol oxidation reactor R0101 and formaldehyde absorption tower T0101; the trioxane synthesis reactor R0201 and trioxane concentration tower T0201; the trioxane refinement reactor R0301, trioxane dehydration membrane module M0301, and trioxane dealcoholization tower T0301, and the recovery and reactive distillation tower T0401.

In the methanol oxidation reactor R0101, a mixture of methanol and methylal (a methanol stream 2 and a circulated stream 14) was subjected to evaporation, mixed with air (a material 1), and then subjected to a reaction under the action of an iron-molybdenum oxidation catalyst at 260° C. and atmospheric pressure to produce formaldehyde, and the formaldehyde was absorbed by a water stream 3 in the formaldehyde absorption tower T0101 to obtain a formaldehyde aqueous solution. The formaldehyde aqueous solution was mixed with the formaldehyde aqueous solution stream 6 (methanol: 0.67%, formaldehyde: 59.02%, water 40.15%, and formic acid: 0.15%) at a bottom of the trioxane concentration tower to obtain a trioxane synthesis stream 4 (methanol: 0.83%, formaldehyde: 59.15%, water: 39.92%, and formic acid: 0.10%).

A ZSM-5 molecular sieve catalyst was pre-filled in the trioxane synthesis reactor R0201 at an amount 10% of a mass of a reaction solution, and the trioxane synthesis stream 4 quickly reached a reaction equilibrium under the action of the ZSM-5 molecular sieve catalyst at 108° C. and atmospheric pressure. Because a trioxane concentration in a gas phase was higher than a trioxane concentration in a liquid phase in the reactor and the gas phase was collected from an outlet, the reaction proceeded in a positive reaction direction. A gas phase stream 5 collected from the outlet of the trioxane synthesis reactor was composed of methanol: 0.51%, formaldehyde: 40.07%, water: 39.92%, trioxane: 19.19%, methyl formate: 0.05%, methylal: 0.13%, and formic acid: 0.10%. The methanol, methyl formate, methylal, and formic acid were by-products of the trioxane synthesis reaction, and the formaldehyde was an unreacted raw material.

The gas phase stream 5 collected from the outlet of the trioxane synthesis reactor was subjected to separation in the trioxane concentration tower T0201 with 20 plates, a reflux ratio of 4, and an operating pressure of −0.010 MPa to obtain a trioxane concentrate stream 7 at a top of the POM concentration tower. The trioxane concentrate stream was composed of methanol: 0.24%, formaldehyde: 4.75%, water: 39.56%, trioxane 54.84%, methyl formate: 0.14%, methylal: 0.37%, and formic acid: 0.10%, and the composition was similar to a composition of a ternary azeotrope of trioxane, formaldehyde, and water. The formaldehyde aqueous solution stream 6 obtained from the trioxane concentration tower was composed of methanol: 0.67%, formaldehyde: 59.02%, water: 40.15%, and formic acid: 0.15%. The stream was returned to the trioxane synthesis reactor R0201.

The trioxane concentrate stream 7 including by-products and unreacted formaldehyde was subjected to catalytic refinement under a hydrogen atmosphere in a fixed bed reactor, such that methyl formate, methylal, formic acid, and formaldehyde were converted into methanol under the action of the $Ni/Al_2O_3$ refinement catalyst, with a reaction pressure of 2.0 MPa, a reaction temperature of 120° C., a liquid space velocity of 1.0 $h^{-1}$, and a hydrogen space velocity of 50 $h^{-1}$. After the catalytic refinement, a refined trioxane stream 8 composed of 5.97% of methanol, 39.41% of water, and 54.63% of paraformaldehyde was obtained for separation.

In the trioxane dehydration membrane module M0301, the refined trioxane stream 8 was subjected to pervaporation through a NaA molecular sieve membrane with a dehydration temperature of 110° C., a pressure of 0.2 MPa at a retentate side, and a pressure of −0.095 MPa at a permeate side to obtain a water-free trioxane mixture stream 10 composed of 10.16% of methanol and 89.84% of trioxane at a retentate side and a water-based permeate stream 9 composed of 4.49% of trioxane and 95.51% of water at a permeate side.

The water-free trioxane mixture stream 10 entered the trioxane dealcoholization tower T0301 for methanol separation to obtain a pure trioxane stream with an impurity content of less than 100 ppm at a bottom of the trioxane dealcoholization tower and a trioxane-containing methanol solution stream 12 composed of 12.83% of trioxane and 87.18% of methanol at a top of the trioxane dealcoholization tower. The trioxane dealcoholization tower had 15 plates, a reflux ratio of 2, a temperature of 112° C. at the bottom of the tower, and an atmospheric pressure.

The trioxane-containing methanol solution stream 12 and the permeate stream 9 were mixed and then allowed to pass through the recovery and reactive distillation tower R0401 with 18 plates, a reflux ratio of 2, a temperature of 120° C., a pressure of 0.05 MPa, and a macroporous resin catalyst to obtain a mixture stream 14 of methanol and methylal at a top of the recovery and reactive distillation tower, which was composed of 1.97% of methanol and 98.03% of methylal. This stream was returned to an inlet of the methanol oxidation reactor and then recycled as a raw material for formaldehyde production. A pure water stream 13 was obtained at a bottom of the recovery and reactive distillation tower, which could be recycled as an absorption liquid of the formaldehyde absorption tower.

Comparative Example 1

Trioxane was prepared by a technique commonly used in the prior art.

A hemiformal concentrate A was prepared in a hemiformal production device.

600 ml of the hemiformal concentrate A was fed into an autoclave equipped with a 1 L pressure-resistant vessel, and then formaldehyde was continuously added from the outside. In addition, nitrogen was fed as a carrier gas into the autoclave at a constant flow rate (50 ml/min to 100 ml/min).

The hemiformal concentrate was subjected to a pyrolysis reaction at a liquid temperature of 160° C. to 170° C. in the autoclave to obtain a mixed gas of a formaldehyde gas and nitrogen. The flow rate of nitrogen and the pyrolysis temperature were appropriately adjusted such that a molar ratio of the formaldehyde gas to the nitrogen in the mixed gas was higher than 70:30.

The formaldehyde gas obtained from the pyrolysis of the hemiformal concentrate A was allowed to contact a solid acidic catalyst, such that the formaldehyde gas was subjected to trimerization to obtain trioxane. A trioxane generator was a fixed bed reactor with an inner diameter of 30 mmφ, which was filled with 135 g of a pre-prepared solid acidic catalyst and flowed through a jacket. A temperature outside a reaction tube was raised to 100° C. The formaldehyde gas was continuously supplied to the fixed bed reactor filled with the solid acidic catalyst A1 through a downward flow. A reaction product gas was continuously discharged to an outside of the trioxane generator through an SUS316 tube maintained at about 125° C., and further guided to a separation device.

A packed tower with a jacketed double tube (about 25 mmφ) was adopted as the separation device. The reaction product gas was continuously supplied from a lower part of the double tube, and benzene was supplied from an upper part at a flow rate of 200 ml/h, such that the reaction product gas and the benzene were in alternating contact. The gaseous trioxane was absorbed by benzene and discharged from a bottom of the packed tower in a liquid phase. The unreacted formaldehyde gas was discharged from an upper part of the packed tower in a gaseous state without being absorbed by benzene. A temperature in the packed tower was adjusted to 30° C. by cooling water flowing through the jacket.

The unreacted formaldehyde gas discharged from the upper part of the packed tower was returned to the trioxane generator.

TABLE 1

Compositions of the trioxane products obtained

| | Example 1 | Comparative Example 1 |
|---|---|---|
| MeOH (ppm) | 40 | 40 |
| $CH_3O(CH_2O)_2CH_3$ (ppm) | 30 | 80 |
| Benzene (ppm) | 0 | 100 |
| TOX (ppm) | >99.99 | >99.97 |
| TOX yield (%) | 31.4 | 30.4 |
| TOX selectivity (%) | 98.5 | 97.2 |

It can be seen from Table 1 that, compared with Comparative Example 1, in Example 1 of the present disclosure, the yield and purity of the trioxane product are both improved. In the present disclosure, impurities such as formaldehyde, formic acid, methyl formate, methylal, and formaldehyde polymer are converted into methanol through catalytic refinement to achieve the purposes of aldehyde removal, acid removal, and ester removal, such that the subsequent separation operation is easy, which increases the reaction conversion rate, optimizes the preparation process of trioxane, and improves the raw material utilization of the entire system and the purity of a trioxane product.

The present disclosure solves the problem that many by-products difficult to separate are produced in a trioxane synthesis process, and reduces an impurity content to improve the purity and quality of a trioxane product. The production of diluted aldehyde solution in the separation process is avoided through refinement, and through the combination with a membrane separation technology, the separation efficiency is improved. The utilization of raw materials in the entire process is improved by adopting a circulating process.

The present disclosure provides a trioxane synthesis process, where impurities such as formaldehyde, formic acid, methyl formate, methylal, and formaldehyde polymer are converted into methanol through catalytic refinement, which achieves the purposes of aldehyde removal, acid removal, and ester removal and makes the subsequent separation operation easy.

The present disclosure avoids the blockage of pipelines and equipment such as rectification tower in the subsequent separation process, reduces the corrosion to subsequent pipelines and equipment, and avoids the occurrence of a multi-component azeotrope in the system.

Compared with the traditional absorption, adsorption, and extraction processes, the catalytic refinement process in the present disclosure leads to no waste liquids and solids, and is environmentally friendly. Moreover, formaldehyde, formic acid, and methyl formate are converted into methanol through the catalytic refinement, and the methanol is then used for formaldehyde production, which improves the atomic utilization. In addition, no diluted aldehyde solution is produced in the entire process, which avoids the disadvantages of high energy consumption and heavy pollution caused by the recovery of diluted aldehyde solution.

In the description of this specification, the description of the terms "one embodiment/implementation", "some embodiments/implementations", "example", "specific example", or "some examples" means that the specific features, structures, materials, or characteristics described with reference to the embodiment/implementation or example are included in at least one embodiment/implementation or example of the present disclosure. In this specification, the illustrative expressions of the above terms are not intended to refer to the same embodiment/implementation or example. Moreover, the particular features, structures, materials, or characteristics described may be combined in any suitable manner in any one or more embodiments/implementations or examples. In addition, those skilled in the art may combine different embodiments/implementations or examples described herein or features in different embodiments/implementations or examples without any contradiction.

Moreover, the terms such as "first" and "second" are used only for the purpose of description and should not be construed as indicating or implying a relative importance, or implicitly indicating a quantity of indicated technical features. Therefore, features defined by "first" and "second" may explicitly or implicitly include at least one of the features. In the description of the present disclosure, "a plurality of" means at least two, such as two or three, unless otherwise clearly and specifically limited.

Those skilled in the art should understand that the foregoing implementations are merely intended to describe the present disclosure clearly, rather than to limit the scope of the present disclosure. Those skilled in the art may make other changes or modifications based on the present disclosure, but these changes or modifications should fall within the scope of the present disclosure.

What is claimed is:

1. A process for preparing trioxane from methanol, comprising:

step 1: subjecting a mixture of methanol and methylal to a reaction under an action of an oxidation catalyst to obtain formaldehyde, and absorbing the formaldehyde with water to obtain a concentrated formaldehyde aqueous solution;

step 2: in a trioxane synthesis reactor, subjecting the concentrated formaldehyde aqueous solution to a cyclization under an action of a cyclization catalyst to obtain a mixture containing trioxane, and passing the mixture containing trioxane through a trioxane concentration tower to obtain a crude trioxane product;

step 3: converting a by-product and unreacted formaldehyde in the crude trioxane product into methanol through a catalytic refinement, conducting a dehydration through a membrane dehydration process, and subjecting a retentate to a dealcoholization to obtain purified trioxane; and step 4: after the purified trioxane is separated, combining remaining streams of an entire process to obtain a mixture comprising methanol, water, and a predetermined amount of trioxane, and subjecting the mixture comprising methanol, water, and a predetermined amount of trioxane to a reactive distillation to obtain a mixture of methanol and methylal at a top of a reactive distillation tower and water at a bottom of the reactive distillation tower; returning the mixture of methanol and methylal to step 1; and returning the water to a formaldehyde absorption tower, or discharging the water from a system.

2. The process according to claim 1, wherein in step 2, the cyclization under the action of the cyclization catalyst is conducted at a reaction temperature of 80° C. to 150° C. and a reaction pressure of −0.1 MPa to 0.3 MPa.

3. The process according to claim 1, wherein in step 2, the cyclization catalyst is an acidic catalyst, the acidic catalyst is a solid acidic catalyst, and the solid acidic catalyst is one or more selected from the group consisting of a resin, a molecular sieve, a supported ionic liquid, and aluminum oxide.

4. The process according to claim 3, wherein in step 2, an amount of the cyclization catalyst is 0.1% to 20% of an amount of a reaction solution.

5. The process according to claim 1, wherein in step 3, the catalytic refinement is conducted with a refinement catalyst, and the refinement catalyst has an acidic site and a hydrogenation active site; and the catalytic refinement is conducted at a reaction temperature of 30° C. to 200° C., a reaction pressure of 0 MPa to 5, and a reaction space velocity of 0.1 $h^{-1}$ to 10 $h^{-1}$.

6. The process according to claim 1, wherein in step 3, under a hydrogen atmosphere, the by-product and the unreacted formaldehyde in the crude trioxane product are converted into the methanol through the catalytic refinement.

7. The process according to claim 1, wherein in step 3, after the catalytic refinement, a refined trioxane stream is subjected to the dehydration with a membrane module, the dehydration is conducted through a pervaporation or a steam permeation, such that a mixture of trioxane and methanol with a water content of less than 0.1% is obtained at a retentate side.

8. The process according to claim 1, wherein in step 3, a membrane used in the membrane dehydration process is a water-permeable molecular sieve membrane; the dehydration at a retentate side is conducted at a temperature of 80° C. to 150° C. and a dehydration pressure of 0.1 MPa to 1.0 MPa; and a pressure at a permeate side is −0.05 MPa to −0.1 MPa.

9. The process according to claim 1, wherein in step 4, the reactive distillation is conducted in a recovery and reactive distillation tower; and a reactor is integrated with the recovery and reactive distillation tower and arranged at a bottom of or inside the recovery and reactive distillation tower, and a volume space velocity of feeding is 0.5 $h^{-1}$ to 50 $h^{-1}$.

* * * * *